United States Patent
Park et al.

(10) Patent No.: US 10,738,362 B2
(45) Date of Patent: Aug. 11, 2020

(54) DETERMINING PROSTATE CANCER RECURRENCE USING POLYMORPHISMS IN ANGIOGENESIS-RELATED GENES

(71) Applicant: H. LEE MOFFITT CANCER CENTER AND RESEARCH INSTITUTE, INC., Tampa, FL (US)

(72) Inventors: Jong Park, Tampa, FL (US); Thomas Sellers, Tampa, FL (US); Julio M. Powsang, Tampa, FL (US); Hui-Yi Lin, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 15/292,742

(22) Filed: Oct. 13, 2016

(65) Prior Publication Data
US 2017/0029902 A1 Feb. 2, 2017

Related U.S. Application Data

(63) Continuation of application No. 14/399,266, filed as application No. PCT/US2013/040337 on May 9, 2013, now abandoned.

(60) Provisional application No. 61/644,572, filed on May 9, 2012, provisional application No. 61/720,557, filed on Oct. 31, 2012.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

2003/0092019 A1   5/2003   Meyer

OTHER PUBLICATIONS

DbSNP rs2173115 (http://www.ncbi.nlm.nih.gov/projects/SNP/snp_ref.cgi?rs=2173115, downloaded Apr. 8, 2016).*
Affymetrix Show results Human Mapping 500K array set (https://www.affymetrix.com/analysis/netaffx/showresults.affx, Mar. 13, 2018).*
Affymetrix Human Mapping 500K array (https://www.affymetrix.com/analysis/netaffx/mappingfullrecord.affx?pk=Mendel_Sty:SNP_A-4254642, Mar. 13, 2018).*
Liu et al (Genes, Chromosomes & cancer (2007) vol. 46, pp. 972-980).*
Wurmbach (Anticancer research (2000) vol. 250, pp. 5217-5220).*
Non-final Office action issued in U.S. Appl. No. 14/399,266 dated Apr. 14, 2016.
Hirschhorn et al. (Genetics in Medicine. vol. 4, No. 2, pp. 45-61, Mar. 2020).
Ioannidis (Nature Genetics, vol. 29, pp. 306-309, Nov. 2001).
Hegele (Arterioscler Thromb Vasc Biol. 2002, 22: 1058-1061).
Pennisi (E. Science (1998) vol. 281, No. 5384, pp. 1787-1789).
Benner et al. (Trends in Genetics (2001) vol. 17, pp. 414-418).
May et al. (Science (1998) vol. 241, p. 1441).
ANGPT1 (http://www.genecards.org/cgi-bin/carddisp.pl?gene=ANGPT1&keywords=angpt1, downloaded Apr. 11, 2016).
DbSNP rs198605(http://www.ncbi.nim.nih.gov/projects/SNP/snp_ref.cgi?rs=198605, downloaded Apr. 8, 2016).
Young (PLOS one (2009) vol. 4, e5302).
Of Cunningham (Cancer Epidemiol Biomarkers (2008) vol. 17, 1781-9).

* cited by examiner

*Primary Examiner* — Steven Pohnert
(74) *Attorney, Agent, or Firm* — Meunier Carlin & Curfman LLC

(57) ABSTRACT

In particular, disclosed is a method for treating a patient with prostate cancer that involves genotyping a nucleic acid sample from the subject for one or more single nucleotide polymorphism (SNP) alleles in one or more genes angiogenesis, comparing the one or more SNP alleles to control allele frequencies to produce a SNP signature, and analyzing the SNP signature to generate a risk score. The risk score can represent the likelihood that the patient's prostate cancer will recur following radical prostatectomy. In particular embodiments, a high risk score in a patient with positive margins is an indication of a high risk of prostate cancer recurrence.

3 Claims, 1 Drawing Sheet

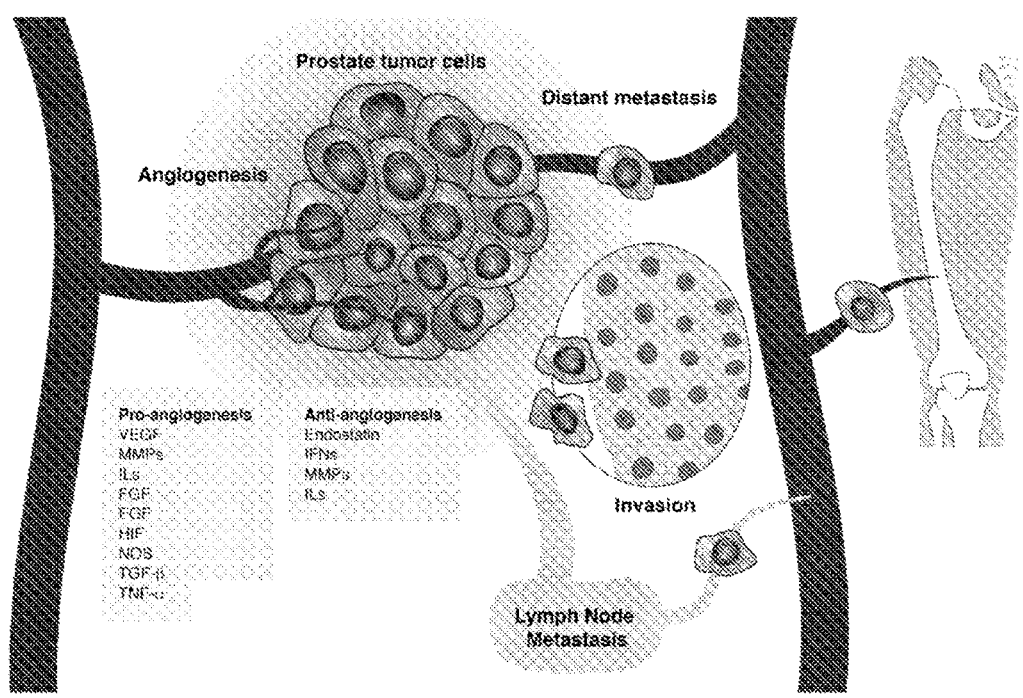

DETERMINING PROSTATE CANCER RECURRENCE USING POLYMORPHISMS IN ANGIOGENESIS-RELATED GENES

CROSS-REFERENCE TO RELATED APPLICATIONS

This application is a continuation of U.S. application Ser. No. 14/399,266, filed May 9, 2013, which claims benefit of U.S. Provisional Application No. 61/644,572, filed May 9, 2012, and U.S. Provisional Application No. 61/720,557, filed Oct. 31, 2012, which are hereby incorporated herein by reference in their entirety.

STATEMENT REGARDING FEDERALLY SPONSORED RESEARCH OR DEVELOPMENT

This invention was made with Government Support under Agreement CA128813 awarded by the National Institutes of Health. The Government has certain rights in the invention.

BACKGROUND

Approximately 20-30% of prostate cancer patients who undergo radical prostatectomy (RP) develop tumor recurrence, but current clinical indicators do not fully account for the varied outcomes associated with RP. Therefore, biomarkers are needed to better predict the outcome of prostate cancer after RP.

SUMMARY

Biomarkers, methods, assays, and kits are provided for prognosing and treating prostate cancer in a patient. The assays and kits can contain primers, probes, or binding agents for detecting SNP alleles listed in Table 2.

In particular, disclosed is a method for treating a patient with prostate cancer that involves genotyping a nucleic acid sample from the subject for one or more single nucleotide polymorphism (SNP) alleles in one or more angiogenesis genes, comparing the one or more SNP alleles to control allele frequencies to produce a SNP signature, and analyzing the SNP signature to generate a risk score. For example, the SNP signature can be analyzed by multivariate regression analysis or principal component analysis to calculate the risk score.

The risk score can represent the likelihood that the patient's prostate cancer will recur following radical prostatectomy. In particular embodiments, a high risk score in a patient with positive margins is an indication of a high risk of prostate cancer recurrence. Therefore, the method can involve prescribing adjuvant therapy if the patient has a high risk score for recurrence, and not prescribing adjuvant therapy if the patient has a low risk score for recurrence. For example, the method can involve prescribing adjuvant radiation therapy for a patient who will have or has had radical prostatectomy. This is particularly useful if the patient has positive margins following the radical prostatectomy.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is an image depicting the role of angiogenesis in prostate tumors.

DETAILED DESCRIPTION

Biomarkers, methods, assays, and kits are provided for determining the prognosis of, and treating a patient with, prostate cancer. In some embodiments, the disclosed methods relate to any primary cancer in the prostate. The prostate cancer can also be a secondary cancer, i.e., cancer cells that metastasized from the prostate to other tissue, or cancer cells metastasized from other tissue into the prostate.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Tumor stage, Gleason score, metastasis and survival in prostate cancer have been associated with angiogenesis, which is an important pathway for tumor progression and metastasis. Angiogenesis is regulated by both activator and inhibitor molecules. Normally, the inhibitors predominate, blocking growth. Should a need for new blood vessels arise, angiogenesis activators increase in number and inhibitors decrease. This prompts the growth and division of vascular endothelial cells and, ultimately, the formation of new blood vessels. Single nucleotide polymorphisms (SNPs) in angiogenesis genes are shown herein to be associated with prostate cancer recurrence. 2,981 SNPs in 547 angiogenesis genes were genotyped and associations between SNP and recurrence-free survival evaluated using Cox regression models to estimate hazard ratios (HR) and 95% confidence intervals (95% CI) under the dominant, recessive, and log-additive inheritance models. Associations were for several families of genes, such as angiopoietins (ANGPT), cadherins (CDH), fibroblast growth factor and its receptor (FGF/FGFR), insulin-like growth factor (IGF), interleukins (IL), metalloproteinases (MMP) and thrombospondin (THBS).

The disclosed method can therefore involve genotyping a biological sample from the patient for SNPs in angiogenesis genes. The method can involve assaying a sufficient number of SNPs to provide a statistically significant risk score, as described below. For example, the method can involve assaying the biological sample from the patient for at least 2, 5, 10, 20, 30, 40, 50, or more SNP alleles in angiogenesis genes.

The term "biological sample" refers to a tissue (e.g., tissue biopsy), organ, cell, cell lysate (or lysate fraction), or body fluid from a subject that contains nucleic acid material. In preferred embodiments, the biological sample is a nucleic acid sample derived from peripheral blood, mouth swab, or tissue biopsy.

In some embodiments, the angiogenesis genes can be selected from the group consisting of ANGPT1, CACNA1C, CDH12, CDH13, CDH6, COL4A3, DDI1, ELK3, FBLN1, FGF12, FGF2, FGFR2, FN1, HDAC3, ID3, IGF2, IL16, IL1A, IL6, ITGA9, ITGAV, ITGB2, ITGB3, LECT1, LZTS1, MAP3K7IP2, MMP15, WP16, MMP28, NCOA3, NOS2, NRP1, P2RY5, PDGFRB, PGF, PTK2, ROBO1, RSPO3, SAMD14, STAB1, TEK, TFP1, TGFB2, THBS2, and TYR.

In particular, the method can involve genotyping the nucleic acid sample for one or more SNP alleles at sites selected from the group consisting of rs1005666, rs10174098, rs1047100, rs10498214, rs1050779, rs10805564, rs10827227, rs10955455, rs1113283, rs11149598, rs1131445, rs11868894, rs1250248, rs13027749, rs13326165, rs1393350, rs1433168, rs1433172, rs1460924, rs1467251, rs1555025, rs1654680, rs16876215, rs17506789, rs1960669, rs198605, rs2069832, rs2071373, rs2143491, rs2152066, rs2173115, rs2359192, rs2429127, rs246394, rs2514864, rs267567, rs2796821, rs2912770, rs2912791, rs2916084, rs2981428, rs2981449, rs3209148, rs3759509, rs3768780, rs3783526, rs3788142, rs3842763, rs4416, rs4778641, rs4795090, rs684, rs7044842, rs7102675, rs7171517, rs722527, rs7625555, rs7742668, rs7839832, rs7871178, rs8034928, rs8176418, rs847690, rs859, rs889730, rs903999, rs9283851, and rs958614, where the SNP is identified by reference SNP ("rs") followed by the National Center for Biotechnology Information (NCBI) SNP identification number.

In some embodiments, the patient has an elevated risk score if the nucleic acid sample comprises at least one (A) allele at rs1005666; at least one (A) allele at rs1047100; at least one (G) allele at rs10498214; at least one (C) allele at rs1050779; at least one (A) allele at rs1113283; at least one (G) allele at rs1131445; at least one (G) allele at rs11868894; at least one (C) allele at rs13027749; at least one (A) allele at rs13326165; at least one (A) allele at rs1393350; at least one (A) allele at rs1460924; at least one (A) allele at rs1467251; at least one (A) allele at rs1654680; at least one (A) allele at rs16876215; at least one (G) allele at rs17506789; at least one (A) allele at rs1960669; at least one (C) allele at rs198605; at least one (A) allele at rs2143491; at least one (A) allele at rs2152066; at least one (C) allele at rs2173115; at least one (A) allele at rs2359192; at least one (G) allele at rs2429127; at least one (A) allele at rs246394; at least one (A) allele at rs2514864; at least one (A) allele at rs267567; at least one (A) allele at rs2796821; at least one (C) allele at rs2912770; at least one (A) allele at rs2912791; at least one (A) allele at rs2916084; at least one (A) allele at rs2981449; at least one (A) allele at rs3209148; at least one (A) allele at rs3788142; at least one (G) allele at rs4778641; at least one (G) allele at rs4795090; at least one (A) allele at rs684; at least one (A) allele at rs7102675; at least one (A) allele at rs7171517; at least one (A) allele at rs722527; at least one (A) allele at rs7839832; at least one (G) allele at rs8034928; at least one (A) allele at rs8176418; at least one (G) allele at rs847690; at least one (G) allele at rs859; at least one (A) allele at rs903999; or any combination thereof.

In some embodiments, the patient has a reduced risk score if the nucleic acid sample comprises at least one (G) allele at rs10174098; at least one (G) allele at rs10805564; at least one (A) allele at rs10827227; at least one (C) allele at rs10955455; at least one (A) allele at rs11149598; at least one (A) allele at rs1250248; at least one (G) allele at rs1433168; at least one (A) allele at rs1433172; at least one (A) allele at rs1555025; at least one (A) allele at rs2069832; at least one (G) allele at rs2071373; at least one (A) allele at rs2981428; at least one (A) allele at rs3759509; at least one (A) allele at rs3768780; at least one (A) allele at rs3783526; at least one (A) allele at rs3842763; at least one (A) allele at rs4416; at least one (A) allele at rs7044842; at least one (G) allele at rs7625555; at least one (G) allele at rs7742668; at least one (A) allele at rs7871178; at least one (G) allele at rs889730; at least one (G) allele at rs9283851; at least one (C) allele at and rs958614; or any combination thereof Genotyping Methods of genotyping SNPs are known in the art, and include for example, sequencing exons, introns, 5' untranslated sequences, or 3' untranslated sequences, performing allele-specific hybridization, allele-specific restriction digests, mutation specific polymerase chain reactions (MSPCR), single-stranded conformational polymorphism (SSCP) detection, denaturing high performance liquid chromatography (DHPLC), infrared matrix-assisted laser desorption/ionization (IR-MALDI) mass spectrometry, and combinations thereof.

Genomic DNA generally is used in the analysis of nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from prostate tissue). Routine methods can be used to extract genomic DNA from a blood or tissue sample, including, for example, phenol extraction. Alternatively, genomic DNA can be extracted with kits such as the QIAAMP® Tissue Kit (Qiagen, Chatsworth, Calif.) and the WIZARD® Genomic DNA purification kit (Promega).

An amplification step is typically, but not necessarily, performed before proceeding with the detection method. For example, exons or introns of a gene can be amplified and then directly sequenced. Dye primer sequencing can be used to increase the accuracy of detecting heterozygous samples.

Allele specific hybridization can be used to detect sequence variants, including complete haplotypes of a subject. In practice, samples of DNA or RNA from one or more subjects can be amplified using pairs of primers and the resulting amplification products (i.e., amplicons) can be immobilized on a substrate (e.g., in discrete regions). The amplicons can be detectably-labeled during the PCR amplification process (e.g., using one or more detectably labeled dNTPs) or subsequent to the amplification process using a variety of chemical or enzymatic techniques such as nick-translation. In some embodiments, one of the primers used in the amplification reaction is biotinylated (e.g., at the 5' end of reverse primer) and the resulting biotinylated amplification product is immobilized on an avidin or streptavidin coated substrate. Hybridization conditions are selected such that a nucleic acid probe can specifically bind to the sequence of interest, e.g., a nucleic acid containing the SNP. Such hybridizations typically are performed under high stringency. High stringency conditions can include the use of low ionic strength solutions and high temperatures for washing. For example, high stringency conditions can include hybridization at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. In some embodiments, the probes can be labeled (e.g., fluorescently) to facilitate detection. In some embodiments, the nucleic acid probes that can specifically bind to a corresponding amplicon are immobilized on a substrate in discrete regions, and contacted with detectably labeled amplicons. The binding of a detectably-labeled amplicon to a corresponding probe indicates the presence of the SNP so amplified in the biological sample.

For nucleotide sequence variants that introduce a restriction site, restriction digest with the particular restriction enzyme can differentiate the alleles. For sequence variants that do not alter a common restriction site, mutagenic primers can be designed that introduce a restriction site when the variant allele is present or when the wild type allele is present. A portion of a nucleic acid can be amplified using the mutagenic primer and a wild type primer, followed by digest with the appropriate restriction endonuclease. Alternatively, the restriction analysis can be done directly on unamplified genomic DNA from a subject.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Any of the methods of detecting sequence variants can, optionally, be performed in formats that allow for rapid preparation, processing, and analysis of multiple samples.

The methods described herein can be carried out using a computer programmed to receive data (e.g., data from a chip containing a panel of SNPs, indicating whether a subject contains SNP alleles associated with risk of recurrence). The computer can output for display information related to a subject's SNP signature and associated risk score.

The data may be obtained via any technique that results in an individual receiving data associated with a sample. For example, an individual may obtain the dataset by generating the dataset himself by methods known to those in the art. Alternatively, the dataset may be obtained by receiving a dataset or one or more data values from another individual or entity. For example, a laboratory professional may generate certain data values while another individual, such as a medical professional, may input all or part of the dataset into an analytic process to generate the result.

A number of suitable high throughput formats exist for genotyping SNPs. Generally, such methods involve a logical or physical array of oligonucleotides (e.g., primers or probes), the subject samples, or both. Common array formats include both liquid and solid phase arrays. For example, assays employing liquid phase arrays, e.g., for hybridization of nucleic acids, can be performed in multi-well or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., xMAP® technology from Luminex (Austin, Tex.), the SECTOR® Imager with MULTI-ARRAY® and MULTI-SPOT® technologies from Meso Scale Discovery (Gaithersburg, Md.), the ORCA™ system from Beckman-Coulter, Inc. (Fullerton, Calif.) and the ZYMATE™ systems from Zymark Corporation (Hopkinton, Mass.).

A variety of solid phase arrays can favorably be employed to genotype SNPs in the context of the disclosed methods, assays and kits. Exemplary formats include membrane or filter arrays (e.g., nitrocellulose, nylon), pin arrays, and bead arrays (e.g., in a liquid "slurry"). Typically, oligonucleotide probes corresponding to gene product are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

Statistical Method

From the genotyped SNP alleles, a dataset can be generated and inputted into an analytical classification process that uses the data to classify the biological sample with a risk score.

A risk score can be determined using standard statistical methods, such as multivariate analysis. In some embodiments, the risk score is a regression value, e.g., where a regression value of about 1 (e.g., at least 0.7, 0.8, 0.9, or 1) is a "high" risk score and a regression value of about 0 (e.g., less than 0, 0.1, 0.2, or 0.3) is a "low" risk score.

The gene profile may also be analyzed by principal component analysis to derive a risk score. Principal component analysis (PCA) is a mathematical procedure that uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it be orthogonal to (i.e., uncorrelated with) the preceding components. When used in the disclosed methods, a PCA score can be a numeric value that summarizes the SNP signature of the entire panel (e.g., Table 2) for that patient's biological sample. Therefore, in these embodiments, a "high" risk score may be a PCA score above the median value, and a "low" risk score may be a PCA score below the median value.

In some embodiments, the gene expression values involve numerous data points that are best managed and stored in a computer readable form. Therefore, in preferred embodiments, the risk score is a regression value derived from the SNP signature as a weighted function of the risk associated with each SNP allele. The weighted function can be derived from linear regression analysis of experimental results comparing SNP signatures of patients with a good prognosis versus those with poor prognosis. Each gene expression value species can be multiplied by a weighting constant and summed.

The analytic classification process may be any type of learning algorithm with defined parameters, or in other words, a predictive model. In general, the analytical process will be in the form of a model generated by a statistical analytical method such as those described below. Examples of such analytical processes may include a linear algorithm, a quadratic algorithm, a polynomial algorithm, a decision tree algorithm, or a voting algorithm.

Using any suitable learning algorithm, an appropriate reference or training dataset can be used to determine the parameters of the analytical process to be used for classification, i.e., develop a predictive model. The reference or training dataset to be used will depend on the desired classification to be determined. The dataset may include data from two, three, four or more classes.

The number of features that may be used by an analytical process to classify a test subject with adequate certainty is 2 or more. In some embodiments, it is 3 or more, 4 or more, 10 or more, or between 10 and 200. Depending on the degree of certainty sought, however, the number of features used in an analytical process can be more or less, but in all cases is at least 2. In one embodiment, the number of features that may be used by an analytical process to classify a test subject is optimized to allow a classification of a test subject with high certainty.

Suitable data analysis algorithms are known in the art. In one embodiment, a data analysis algorithm of the disclosure comprises Classification and Regression Tree (CART), Multiple Additive Regression Tree (MART), Prediction Analysis for Microarrays (PAM), or Random Forest analysis. In other embodiments, a data analysis algorithm of the disclosure comprises ANOVA and nonparametric equivalents, linear discriminant analysis, logistic regression analysis, nearest neighbor classifier analysis, neural networks, principal component analysis, hierarchical cluster analysis, quadratic discriminant analysis, regression classifiers and support vector machines.

Adjuvant Therapy

The calculated risk score can represent the likelihood that the patient's prostate cancer will recur, e.g., following radical prostatectomy. Therefore, the method can involve prescribing adjuvant therapy if the patient has a high risk score for recurrence, and not prescribing adjuvant therapy if the patient has a low risk score for recurrence.

The term "adjuvant therapy" refers to a treatment used after primary treatments, such as surgery or radiation. Examples of adjuvant therapy include chemotherapy, hormone therapy, radiation therapy, immunotherapy, and targeted therapy. The role of adjuvant therapy is to increase the cure rate of traditional therapies, such as surgery or radiation. By definition, adjuvant therapy is utilized prior to the documentation of persistent disease. That is, it is administered either before (neoadjuvant), concomitant with, or soon after the primary therapeutic strategy, without evidence (such as an elevated PSA level) of recurring disease. The argument for adjuvant therapy is that it extends the therapeutic margin of conventional therapy, which may be achieved by obliterating either microscopic deposits of cancer outside the surgical/radiation field or subclinical metastatic disease.

Generally, prostate cancer relapse can be detected with PSA when the disease is still microscopic. On average, scan-detected metastases appear more than ten years after a PSA relapse occurs. However, there are two exceptions to the rule that PSA always rises before cancer is known to be present. One is when margins are positive after surgery, and the second is when biopsies are positive after radiation. In the former case, the amount of persistent disease after surgery is so small that PSA fails to register. In the latter case, PSA production from residual prostate gland "overshadows" the small amount of PSA coming from cancer.

In particular embodiments, a high risk score in a patient with positive margins is an indication of a high risk of prostate cancer recurrence. Positive margins occur after surgery in 10% to 50% of men (the percentage depends on patient variables and surgeon skill). Positive margins are common because the prostate is only a few millimeters from the bladder and rectum. Even the finest surgeon must leave cancer behind if the cancer invades outside the gland. Cutting into the bladder or rectum is not an option. Positive margins are reported a couple days after the operation by a pathologist who specializes in examining the gland under the microscope. When a positive margin occurs, the risk of PSA Relapse is 50%.

In particular embodiments, the method involves prescribing adjuvant radiation therapy after radical prostatectomy if the patient has a high risk score for recurrence. Radiation is the most common treatment for a local relapse after surgery. When surgical margins are positive radiation to the prostate fossa, the location of where the prostate used to be, lowers PSA relapse rates and modestly improves the ten-year survival rate. However, the possibility of microscopic metastases needs to be considered since radiation to the fossa alone will fail if cancer is present in other parts of the body. Microscopic metastases are suspected more strongly when the Gleason score is high and when the rate of PSA rise is brisk. In some embodiments, a high recurrence risk score is also an indication of a higher risk of metastases. When suspicions are high, additional radiation to the lymph nodes in combination with testosterone inactivating pharmaceuticals (TIP) should be considered. Therefore, in some embodiments, a patient with a high risk score is prescribed a combination adjuvant therapy, such as radiation and hormone therapy.

A number of embodiments of the invention have been described. Nevertheless, it will be understood that various modifications may be made without departing from the spirit and scope of the invention. Accordingly, other embodiments are within the scope of the following claims.

EXAMPLES

Example 1

In a historical cohort of 1,061 prostatectomy cases treated at the Moffitt Cancer Center from 1986 to 2003, 311 recurrent (biochemical and/or clinical recurrence) cases and 750 non-recurrent cases (non-recurrent prostate cancer patients were identified who had a radical prostatectomy at Moffitt Cancer Center between 1986 and 2003). A recurrent case was defined by an elevated PSA level after surgery, clinical metastasis or disease specific death.

The selected characteristics of the subjects is shown in Table 1 below:

TABLE 1

| Characteristics | [a]Non-recurrent (n = 942) | [a]Recurrent (n = 297) | P-value |
|---|---|---|---|
| Age at diagnosis (mean ± std) | 59.3 ± 7.3 | 61.9 ± 7.5 | <0.0001 |
| Gleason (n, %) | | | |
| 2-6 | 564 (65.2) | 92 (41.8) | <0.0001 |
| 7 | 277 (32.0) | 96 (43.6) | |
| >7 | 24 (2.8) | 32 (14.6) | |
| Stage (n, %) | | | |
| 1&2 | 730 (98.9) | 177 (93.2) | <0.0001 |
| 3&4 | 8 (1.1) | 13 (6.8) | |

[a]Recurrence by defined as either elevated PSA level after surgical treatment, clinical metastasis or disease specific death 2,981 SNPs were genotyped in 547 angiogenesis genes and associations evaluated between SNP and recurrence-free survival using Cox regression models to estimate hazard ratios (HR) and 95% confidence intervals (95% CI) under the dominant, recessive and log-additive inheritance models. The HR therefore represents the risk for recurrence for a subject having the SNP minor allele.

Genotyping was performed using the Illumina Golden-Gate™ assay at the Molecular Genomic Core at the Moffitt Cancer Center. SNP call rate>90%, sample call rate>90% and concordance between duplicate samples >98%. q-values were The calculated to estimate false discovery rates to control for multiple testing.

The mean age at diagnosis of the study subjects was 59.7 (SD=7.5) years. The recurrence rate was 29.3% with a median recurrence-free survival of 200.8 (range=179.0-241.9) months. A total of 67 SNPs in 44 angiogenesis genes had raw P values<0.01. 33 SNPs in 20 genes had raw p-values<0.005.

Associations were found for several families of genes that have been previously associated with aggressiveness and/or survival of prostate cancer, such as angiopoietins (ANGP cadherins (CDH), fibroblast growth factor and its receptor (FGF/FGFR), insulin-like growth factor (IGF), interleukins (IL), metalloproteinases (WP) and thrombospondin (THBS). Results are shown in Table 2.

TABLE 2

| marker | Gene | Gene | P value | FDR | Model[c] | HR (95% CI)[b] |
|---|---|---|---|---|---|---|
| rs1654680 | ANGPT1 | ANGPT1 | 0.0001 | 0.0207 | Add | 1.68 (1.3-2.17) |
| rs1005666 | HDAC3 | HDAC3 | 0.0084 | 0.0989 | Add | 1.4 (1.09-1.81) |
| rs198605 | P2RY5 | P2RY5 | 0.0002 | 0.0207 | Add | 1.51 (1.22-1.88) |
| rs11149598 | CDH13 | CDH13 | 0.005 | 0.0989 | Dom | 0.65 (0.48-0.88) |
| rs1960669 | FGF2 | FGF2 | 0.0013 | 0.0598 | Rec | 2.69 (1.47-4.92) |
| rs722527 | ELK3 | ELK3 | 0.0072 | 0.0989 | Rec | 2.29 (1.25-4.19) |
| rs7171517 | IL16 | IL16 | 0.0097 | 0.0989 | Dom | 1.38 (1.08-1.75) |
| rs8176418 | TFPI | TFPI | 0.0097 | 0.0989 | Rec | 2.4 (1.24-4.67) |
| rs16876215 | ANGPT1 | ANGPT1 | 0.0063 | 0.0989 | Rec | 2.41 (1.28-4.54) |
| rs11868894 | ITGB3 | ITGB3 | 0.0084 | 0.0989 | Add | 1.32 (1.07-1.63) |
| rs1467251 | MMP16 | MMP16 | 0.0019 | 0.075 | Rec | 2.22 (1.34-3.68) |
| rs4795090 | MMP28 | MMP28 | 0.0095 | 0.0989 | Dom | 1.37 (1.08-1.73) |
| rs13326165 | STAB1 | STAB1 | 0.0058 | 0.0989 | Rec | 1.99 (1.22-3.26) |
| rs1050779 | MMP15 | MMP15 | 0.0095 | 0.0989 | Rec | 1.88 (1.17-3.03) |
| rs1047100 | FGFR2 | FGFR2 | 0.0007 | 0.0446 | Dom | 1.48 (1.18-1.87) |
| rs1460924 | FGF12 | FGF12 | 0.0006 | 0.0414 | Dom | 1.49 (1.19-1.87) |
| rs8034928 | IL16 | IL16 | 0.0093 | 0.0989 | Dom | 1.36 (1.08-1.71) |
| rs3788142 | ITGB2 | ITGB2 | 0.0047 | 0.0989 | Rec | 1.81 (1.2-2.73) |
| rs684 | ITGB2 | ITGB2 | 0.0002 | 0.0207 | Rec | 2.04 (1.4-2.97) |
| rs3768780 | ITGAV | ITGAV | 0.0078 | 0.0989 | Rec | 0.39 (0.19-0.78) |
| rs859 | IL16 | IL16 | 0.0005 | 0.0377 | Add | 1.37 (1.15-1.64) |
| rs1113283 | NOS2 | NOS2 | 0.0073 | 0.0989 | Rec | 1.7 (1.15-2.52) |
| rs1250248 | FN1 | FN1 | 0.004 | 0.0989 | Add | 0.74 (0.6-0.91) |
| rs3842763 | IGF2 | IGF2 | 0.004 | 0.0989 | Add | 0.75 (0.61-0.91) |
| rs2796821 | TGFB2 | TGFB2 | 0.0031 | 0.0988 | Rec | 1.78 (1.22-2.62) |
| rs958614 | CDH12 | CDH12 | 0.008 | 0.0989 | Add | 0.76 (0.62-0.93) |
| rs2912770 | FGFR2 | FGFR2 | 0.0034 | 0.0989 | Dom | 1.41 (1.12-1.78) |
| rs7102675 | DDI1 | DDI1 | 0.0043 | 0.0989 | Dom | 1.4 (1.11-1.77) |
| rs1393350 | TYR | TYR | 0.0052 | 0.0989 | Rec | 1.65 (1.16-2.33) |
| rs17506789 | MAP3K7IP2 | MAP3K7IP2 | 0.0085 | 0.0989 | Add | 1.27 (1.06-1.52) |
| rs847690 | SAMD14 | SAMD14 | 0.0079 | 0.0989 | Rec | 1.6 (1.13-2.28) |
| rs3783526 | IL1A | IL1A | 0.0048 | 0.0989 | Add | 0.77 (0.64-0.92) |
| rs7839832 | PTK2 | PTK2 | 0.008 | 0.0989 | Rec | 1.6 (1.13-2.26) |
| rs10498214 | COL4A3 | COL4A3 | 0.0076 | 0.0989 | Add | 1.26 (1.06-1.5) |
| rs246394 | PDGFRB | PDGFRB | 0.0033 | 0.0989 | Add | 1.3 (1.09-1.54) |
| rs2071373 | IL1A | IL1A | 0.0098 | 0.0989 | Add | 0.79 (0.66-0.94) |
| rs10174098 | ITGAV | ITGAV | 0.0083 | 0.0989 | Rec | 0.53 (0.34-0.85) |
| rs13027749 | ITGAV | ITGAV | 0.0082 | 0.0989 | Dom | 1.4 (1.09-1.79) |
| rs2514864 | ANGPT1 | ANGPT1 | 0.0001 | 0.0207 | Rec | 1.87 (1.36-2.56) |
| rs1131445 | IL16 | IL16 | 0.0008 | 0.0474 | Add | 1.33 (1.13-1.58) |
| rs2916084 | ANGPT1 | ANGPT1 | 0.0043 | 0.0989 | Add | 1.27 (1.08-1.5) |
| rs2359192 | PGF | PGF | 0.0039 | 0.0989 | Add | 1.33 (1.09-1.6) |
| rs1433172 | ANGPT1 | ANGPT1 | 0.0025 | 0.0863 | Dom | 0.7 (0.56-0.88) |
| rs889730 | CDH13 | CDH13 | 0.0018 | 0.0746 | Add | 0.74 (0.61-0.89) |
| rs2143491 | NCOA3 | NCOA3 | 0.0071 | 0.0989 | Dom | 1.39 (1.09-1.77) |
| rs4778641 | IL16 | IL16 | 0.0012 | 0.0598 | Add | 1.33 (1.12-1.58) |
| rs2429127 | CACNA1C | CACNA1C | 0.0058 | 0.0989 | Rec | 1.49 (1.12-1.98) |
| rs10955455 | ANGPT1 | ANGPT1 | 0 | 0 | Dom | 0.62 (0.49-0.78) |

TABLE 2-continued

| | | | | | | | |
|---|---|---|---|---|---|---|---|
| rs10805564 | CDH6 | CDH6 | 0.0041 | 0.0989 | Dom | 0.71 | (0.56-0.9) |
| rs2912791 | FGFR2 | FGFR2 | 0.0078 | 0.0989 | Add | 1.25 | (1.06-1.46) |
| rs2069832 | IL6 | IL6 | 0.0085 | 0.0989 | Dom | 0.73 | (0.57-0.92) |
| rs2981449 | FGFR2 | FGFR2 | 0.0037 | 0.0989 | Rec | 1.49 | (1.14-1.94) |
| rs2152066 | TEK | TEK | 0.0036 | 0.0989 | Dom | 1.63 | (1.17-2.27) |
| rs3759509 | LECT1 | LECT1 | 0.0013 | 0.0598 | Dom | 0.67 | (0.53-0.86) |
| rs9283851 | THBS2 | THBS2 | 0.0086 | 0.0989 | Dom | 0.73 | (0.58-0.92) |
| rs7871178 | TEK | TEK | 0.0047 | 0.0989 | Rec | 0.62 | (0.45-0.86) |
| rs7044842 | TEK | TEK | 0.0088 | 0.0989 | Add | 0.8 | (0.68-0.95) |
| rs10827227 | NRP1 | NRP1 | 0.0089 | 0.0989 | Add | 0.8 | (0.68-0.95) |
| rs1433168 | ANGPT1 | ANGPT1 | 0.0021 | 0.0791 | Add | 0.77 | (0.65-0.91) |
| rs3209148 | FGF12 | FGF12 | 0.0009 | 0.0497 | Dom | 1.58 | (1.21-2.08) |
| rs7742668 | RSPO3 | RSPO3 | 0.01 | 0.0989 | Rec | 0.62 | (0.44-0.89) |
| rs4416 | FBLN1 | FBLN1 | 0.0057 | 0.0989 | Dom | 0.7 | (0.54-0.9) |
| rs2981428 | FGFR2 | FGFR2 | 0.0075 | 0.0989 | Add | 0.8 | (0.67-0.94) |
| rs1555025 | ID3 | ID3 | 0.0083 | 0.0989 | Add | 0.8 | (0.68-0.94) |
| rs267567 | ITGA9 | ITGA9 | 0.0071 | 0.0989 | Dom | 1.49 | (1.11-1.99) |
| rs2173115 | LZTS1 | LZTS1 | 0.0023 | 0.0829 | Rec | 1.48 | (1.15-1.91) |
| rs7625555 | ROBO1 | ROBO1 | 0.0061 | 0.0989 | Rec | 0.63 | (0.46-0.88) |
| rs903999 | LZTS1 | LZTS1 | 0.0029 | 0.0961 | Rec | 1.48 | (1.14-1.91) |

| marker | Gene | Major Allele | Minor Allele | MAF[a] |
|---|---|---|---|---|
| rs1654680 | ANGPT1 | G | A | 0.066322478 |
| rs1005666 | HDAC3 | G | A | 0.074132492 |
| rs198605 | P2RY5 | G | C | 0.084546926 |
| rs11149598 | CDH13 | G | A | 0.129658385 |
| rs1960669 | FGF2 | C | A | 0.134496124 |
| rs722527 | ELK3 | C | A | 0.136434109 |
| rs7171517 | IL16 | G | A | 0.142358417 |
| rs8176418 | TFPI | C | A | 0.147864625 |
| rs16876215 | ANGPT1 | G | A | 0.161478599 |
| rs11868894 | ITGB3 | A | G | 0.173002327 |
| rs1467251 | MMP16 | G | A | 0.175349922 |
| rs4795090 | MMP28 | A | G | 0.176539361 |
| rs13326165 | STAB1 | G | A | 0.193261038 |
| rs1050779 | MMP15 | G | C | 0.196734059 |
| rs1047100 | FGFR2 | G | A | 0.222049689 |
| rs1460924 | FGF12 | C | A | 0.238372093 |
| rs8034928 | IL16 | A | G | 0.240123935 |
| rs3788142 | ITGB2 | G | A | 0.243940579 |
| rs684 | ITGB2 | G | A | 0.247090768 |
| rs3768780 | ITGAV | G | A | 0.253493789 |
| rs859 | IL16 | A | G | 0.253708041 |
| rs1113283 | NOS2 | G | A | 0.25484872 |
| rs1250248 | FN1 | G | A | 0.259483454 |
| rs3842763 | IGF2 | C | A | 0.260108865 |
| rs2796821 | TGFB2 | G | A | 0.260852713 |
| rs958614 | CDH12 | A | C | 0.261496493 |
| rs2912770 | FGFR2 | A | C | 0.267288267 |
| rs7102675 | DDI1 | G | A | 0.273993808 |
| rs1393350 | TYR | G | A | 0.274004684 |
| rs17506789 | MAP3K7IP2 | A | G | 0.288932806 |
| rs847690 | SAMD14 | A | G | 0.293478261 |
| rs3783526 | IL1A | G | A | 0.298837209 |
| rs7839832 | PTK2 | G | A | 0.299298519 |
| rs10498214 | COL4A3 | A | G | 0.303195635 |
| rs246394 | PDGFRB | G | A | 0.30471246 |
| rs2071373 | IL1A | A | G | 0.31124031 |
| rs10174098 | ITGAV | A | G | 0.32192846 |
| rs13027749 | ITGAV | A | C | 0.324729392 |
| rs2514864 | ANGPT1 | G | A | 0.325966851 |
| rs1131445 | IL16 | A | G | 0.332816137 |
| rs2916084 | ANGPT1 | T | A | 0.335015528 |
| rs2359192 | PGF | C | A | 0.337890625 |
| rs1433172 | ANGPT1 | G | A | 0.348179706 |
| rs889730 | CDH13 | A | G | 0.361197512 |
| rs2143491 | NCOA3 | G | A | 0.36377709 |
| rs4778641 | IL16 | A | G | 0.374704492 |
| rs2429127 | CACNA1C | A | G | 0.382422803 |
| rs10955455 | ANGPT1 | A | C | 0.387810559 |
| rs10805564 | CDH6 | A | G | 0.399612403 |
| rs2912791 | FGFR2 | G | A | 0.408844065 |
| rs2069832 | IL6 | G | A | 0.423377639 |
| rs2981449 | FGFR2 | G | A | 0.426470588 |
| rs2152066 | TEK | C | A | 0.432773109 |
| rs3759509 | LECT1 | C | A | 0.436619718 |
| rs9283851 | THBS2 | A | G | 0.437062937 |
| rs7871178 | TEK | G | A | 0.437111801 |

TABLE 2-continued

| | | | | |
|---|---|---|---|---|
| rs7044842 | TEK | G | A | 0.440124417 |
| rs10827227 | NRP1 | G | A | 0.44074361 |
| rs1433168 | ANGPT1 | A | G | 0.442667707 |
| rs3209148 | FGF12 | G | A | 0.443388757 |
| rs7742668 | RSPO3 | A | G | 0.449526814 |
| rs4416 | FBLN1 | G | A | 0.449802372 |
| rs2981428 | FGFR2 | C | A | 0.450194553 |
| rs1555025 | ID3 | C | A | 0.465557276 |
| rs267567 | ITGA9 | G | A | 0.46899841 |
| rs2173115 | LZTS1 | A | C | 0.46979086 |
| rs7625555 | ROBO1 | A | G | 0.493754879 |
| rs903999 | LZTS1 | G | A | 0.49437751 |

[a]Minor allele frequency
[b]Hazard Ratio (95% confidence intervals)
[c]Add, Additive; Dom, Dominant; Rec, Recessive This comprehensive study of angiogenesis genes and prostate cancer suggests that variants in angiogenesis-related genes may influence risk for prostate cancer recurrence and may be used to predict outcome after radical prostatectomy.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a patient with prostate cancer, comprising genotyping a single nucleotide polymorphism (SNP) allele in angiopoietin 1 gene (ANGPT1) in a patient, wherein the SNP allele comprises at least one adenine (A) allele at rs16876215, and administering adjuvant therapy to the patient, wherein the patient is a human patient.

2. The method of claim 1, wherein the patient has undergone radical prostatectomy.

3. The method of claim 2, wherein the patient has positive margins after the radical prostatectomy.

* * * * *